(12) United States Patent
Struck, II

(10) Patent No.: US 8,967,557 B2
(45) Date of Patent: Mar. 3, 2015

(54) LIGHTWEIGHT PORTABLE LAWN CADDY

(76) Inventor: Eloy Struck, II, Bay City, MI (US)

( * ) Notice: Subject to any disclaimer, the term of this patent is extended or adjusted under 35 U.S.C. 154(b) by 70 days.

(21) Appl. No.: 13/478,227

(22) Filed: May 23, 2012

(65) Prior Publication Data
US 2013/0313377 A1 Nov. 28, 2013

(51) Int. Cl.
 B65B 67/04 (2006.01)
 B62B 1/26 (2006.01)
 B62B 3/10 (2006.01)
 B62B 1/00 (2006.01)
 B62B 3/00 (2006.01)

(52) U.S. Cl.
 CPC ............. B62B 1/266 (2013.01); *B62B 3/106* (2013.01); *B62B 1/00* (2013.01); *B62B 2202/50* (2013.01); *B62B 3/00* (2013.01)
 USPC .. 248/99; 280/47.27; 280/47.29; 280/47.131; 414/446; 141/392; 248/98

(58) Field of Classification Search
 USPC .............. 248/97, 98, 99, 100, 129, 145.6; 280/47.24, 47.26, 47.27, 47.131, 280/47.34, 47.35, 47.41, 47.28, 47.29, 651, 280/652, 654; 414/444, 446, 447, 449; 141/10, 390, 391, 392; 224/578
 See application file for complete search history.

(56) References Cited

U.S. PATENT DOCUMENTS

| | | | | |
|---|---|---|---|---|
| 2,455,729 | A * | 12/1948 | Byers | 248/98 |
| 2,520,226 | A * | 8/1950 | Smith | 280/652 |
| 6,994,302 | B1 * | 2/2006 | Simmons | 248/98 |
| 7,014,199 | B2 * | 3/2006 | Hendzel | 280/47.35 |
| 7,686,260 | B1 * | 3/2010 | Tetradis | 248/98 |
| 8,104,778 | B1 * | 1/2012 | Rojas et al. | 280/47.27 |
| 8,479,780 | B2 * | 7/2013 | Fernandez et al. | 141/10 |

\* cited by examiner

*Primary Examiner* — Tan Le

(57) ABSTRACT

A lawn caddy for receiving and transporting waste such as grass clippings, leaves, plant vegetation and compost waste. The lawn caddy transports yard waste from one location to another without heavy lifting. It is light and durable, having a maximum weight of 10 to 12 pounds and can contain up to 40 pounds of waste or less. By filling refuge bags and transporting waste to a curb side shortens time spent in cutting and cleaning lawns.

6 Claims, 6 Drawing Sheets

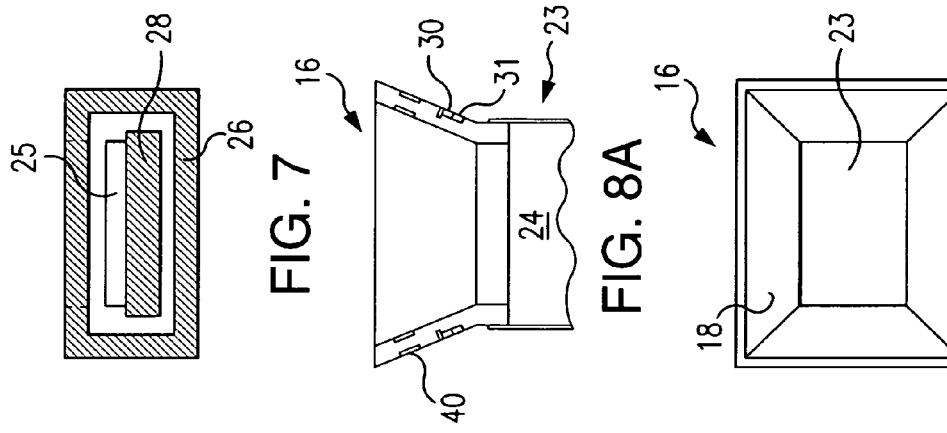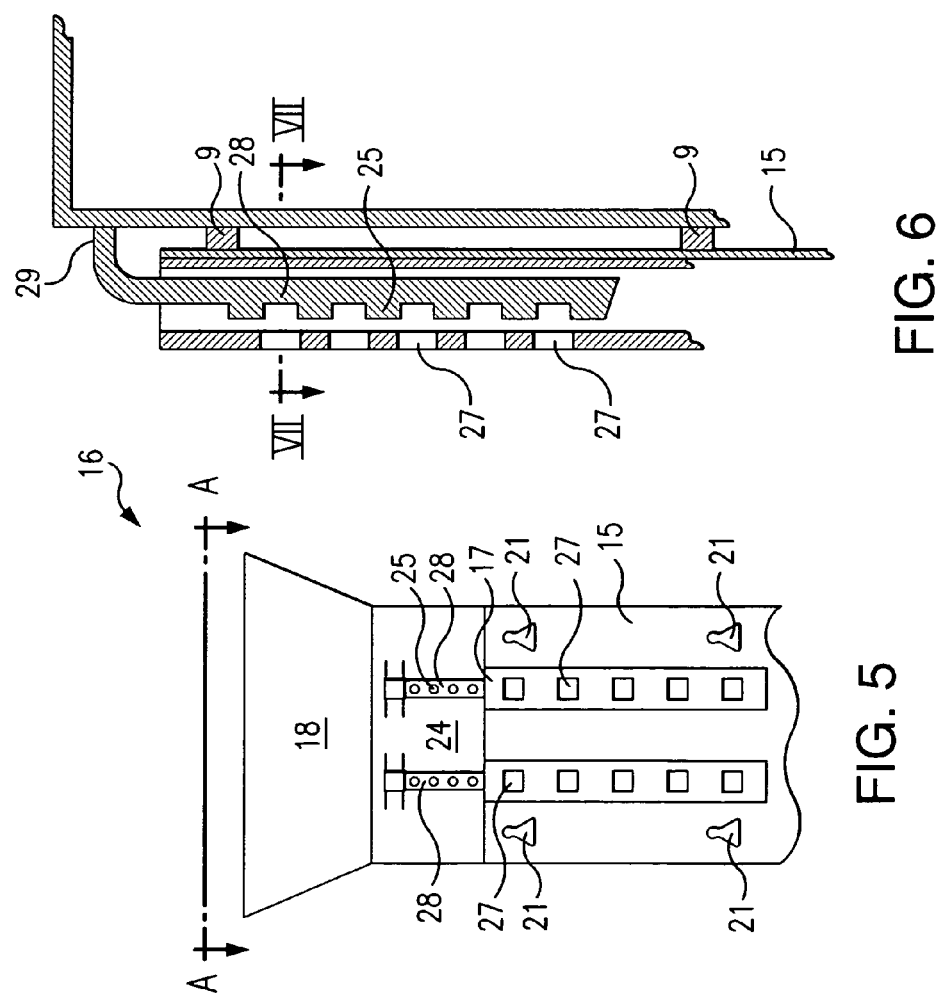

LIGHTWEIGHT PORTABLE LAWN CADDY

BACKGROUND OF THE INVENTION

Lawn service equipment comes in many shapes and sizes. For example, U.S. Pat. No. 6,131,861, issued on Oct. 17, 2000 to Fortier deals with a bag holder having an adjustable frame assembly. U.S. Pat. No. 6,416,713, issued Jul. 9, 2002 to Abrams deals with a rigid liner for yard refuse bags and U.S. Pat. No. 6,659,407 that issued Dec. 9, 2003 to Asaro, deals with a collapsible trash bag stand with punch tab bag retainers.

U.S. Pat. No. 7,731,134, that issued on Jun. 8, 2010 to Mutert deals with a bag stand. U.S. Pat. No. 6,450,461 deals a trash bag holder. U.S. Pat. No. 7,222,825, that issued May 29, 2007 to Gilbert deals with yet another lawn waste bag holder. U.S. Pat. No. 7,686,260 that issued Mar. 30, 2010 to Tetradis deals with a lawn and leaf bag holder. U.S. Pat. No. 8,038,107 that issued on Oct. 18, 2011 to Gains deals with a method of retaining a lawn waste bag in an open position. U.S. Pat. No. 7,850,129 that issued Dec. 14, 2010 to Neuenberger deals with a trash bag holder.

U.S. Pat. No. 7,014,199, that issued on Mar. 21, 2006 to Hendzel deals with an adjustable multiple container deployment cart. U.S. Pat. No. 7,819,407 that issued Oct. 26, 2010 to Charitun deals with a cart for transporting beach accessories. U.S. Pat. No. 7,703,723, issued Apr. 27, 2010 to Cooper, et al that deals with a bag support device. U.S. Pat. No. 6,994,302 that issued Feb. 7, 2006 to Simmons deals with a lawn maintenance system that is comprised of bags on a wheeled cart. U.S. Patent Publication 2003/0218104 that published Nov. 27, 2003 in the name of Klotz deals with a device to hold paper bag for grass clippings, and U.S. design Pat. 556,417 that issued Nov. 27, 2007 deals with a cleaning trolley that apparently holds trash cans.

These prior art devices have unique functions, such as, folding arms, folding legs, dual containers, and they essentially all do a similar process of containing yard waste. Some have some sort of frame to support containers. Some have wheels for transporting lawn debris. Some pack and hold lawn waste. The device of the instant invention has a unique sliding one piece panel track mechanism that attaches to a platform track at the back of the vertical struts, to allow the adjustability of the funnel and bag.

THE INVENTION

Thus, what is disclosed and claimed herein is a portable lawn caddy, the lawn caddy comprising in combination two adjacent, spaced-apart, parallel struts, each said strut having a near end and a distal end, each said strut having a handle at the distal end wherein the distal ends are joined by a flat platform.

The distal ends have an axle through them and each end of the axle is fitted with a rotatable wheel. There is a plurality of cross members extending from one strut to the other strut. There is a back plate mounted near the distal ends of the struts, the back plate having a parallel set of vertical tubular rails attached thereto, each said vertical tubular rail having openings through it, wherein the openings are adjacent and evenly spaced in vertical rows.

There is a removable funnel having a funnel top. The funnel top has bottom edges, and mounted on the bottom edges, there are panels. The panels are configured to provide a box-like structure, said panels having mounted on an outside surface, spring clips for holding a trash bag.

There is a back panel of the box-like structure that has fixedly mounted thereon, parallel, spaced-apart, vertical bars, each said bar having vertical clips attached thereto, said vertical clips aligning in width with the openings in the vertical tubular rails, each said vertical bar being insertable in one of the vertical tubular rails.

There is an adjustable, extendable bar wheel affixed to a middle cross member, at the back of the back plate. The lower edges have mounted thereon, spring clips for holding a trash bag.

In a second embodiment, there is a portable lawn caddy. The lawn caddy comprises in combination two adjacent, spaced-apart, parallel struts. Each strut has a near end and a distal end and each strut has a handle at the distal end.

The distal ends are joined by a flat platform and the distal ends have an axle through them. Each of the ends of the axle is fitted with a rotatable wheel. There is a plurality of cross members extending from one said strut to the other strut.

There is a back plate mounted near the distal ends of the struts, the back plate having a single, essentially centered, vertical tubular rail attached to it. The vertical tubular rail has openings through it, wherein the openings are evenly spaced in a vertical row.

There is a removable funnel having a funnel top. The funnel top has bottom edges, there being mounted on the bottom edges, panels. The panels are configured to provide a box-like structure. The panels have mounted on an outside surface, spring clips for holding a trash bag.

The back panel of the box-like structure has fixedly mounted thereon, a vertical bar, the bar having vertical clips attached to it. The vertical clips align in width with the openings in the vertical tubular rail, the vertical bar being insertable in the vertical tubular rail. There is an adjustable, extendable bar wheel affixed to a middle cross member, at the back of the back plate.

BRIEF DESCRIPTION OF THE DRAWINGS

FIG. 5 is an enlarged portion of the device from the back showing detail of the panel and tracks.

FIG. 6 is an enlargement of a portion of the panel and tracks showing the detail.

FIG. 7 is a full top view of the combination of the bar and the vertical tubular rail.

FIG. 8A is a front view of the funnel.

FIG. 8B is a top view of the funnel.

DETAILED DESCRIPTION OF THE INVENTION

Figure 2:
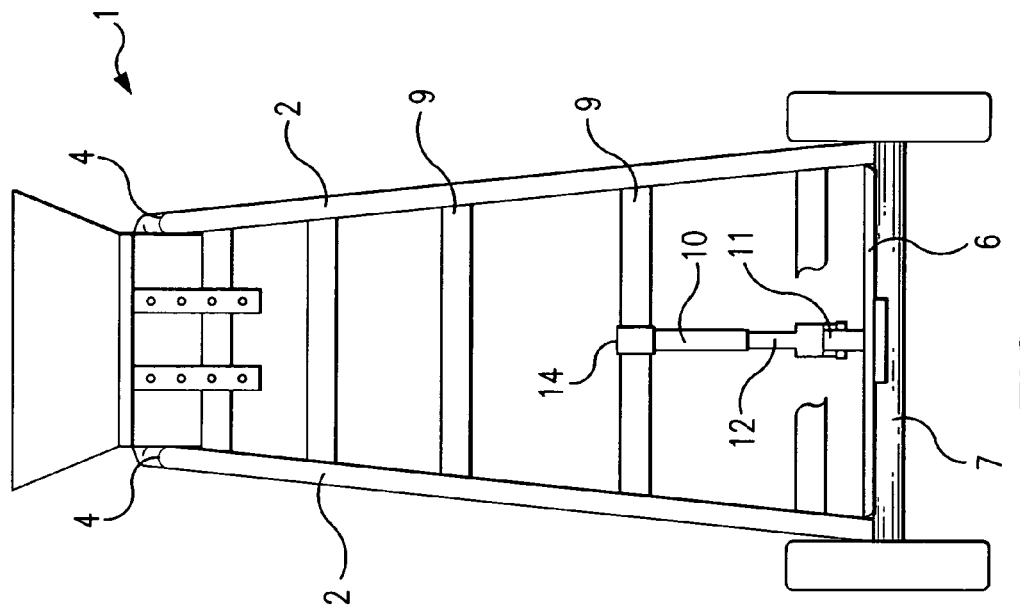
FIG. 2 is a full front view of the device.
Figure 1:
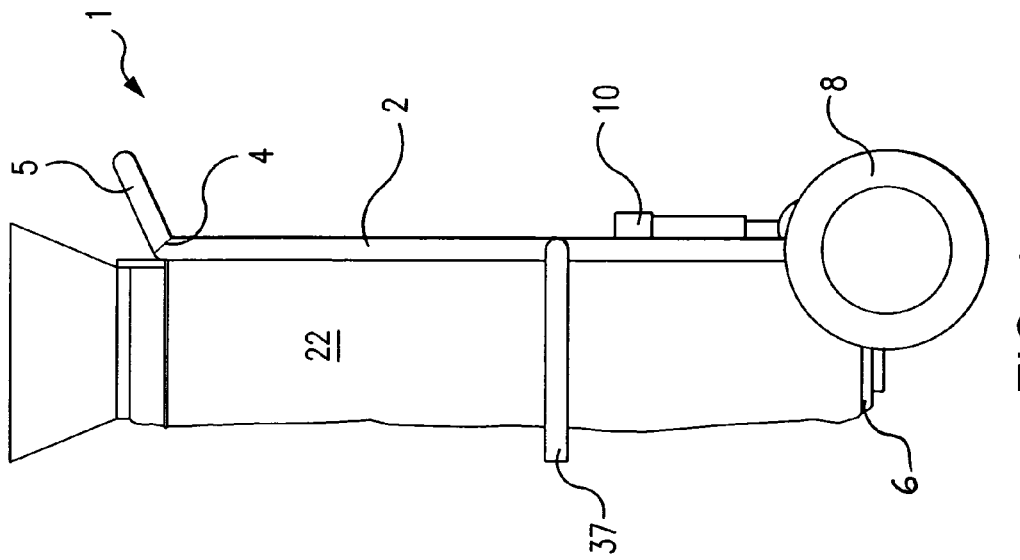
FIG. 1 is a full side view of the device of this invention holding a trash bag and equipped with a funnel.

FIG. 1 is a full side view of a device 1 of this invention and FIG. 2 is a full front view. There is shown two adjacent, space-apart, parallel struts 2 which form a portion of the back of the device 1. Each strut 2 has a distal end 3 and a near end 4, and in the there is shown a handle 5 attached to the near ends 4. The distal ends 3 are attached to a platform 6 (See FIGS. 2 and 13) all of which will be discussed in detail infra. The distal ends 3 of the struts 2 have an axle 7 through them which supports wheels 8. For this invention, the wheels 8 should be at least 3 inches in diameter, but can be larger, and most preferred is 4¾ inches in diameter.

There is a plurality of cross members 9 extending from one strut 2 to the other strut 2 to stabilize the form of the device 1, and also to allow for certain attachments and for holding equipment as will be discussed infra. Although these cross members 9 can be bolted onto the struts 2, it is preferred that such cross members 9 be welded to the struts 2.

Figure 3:
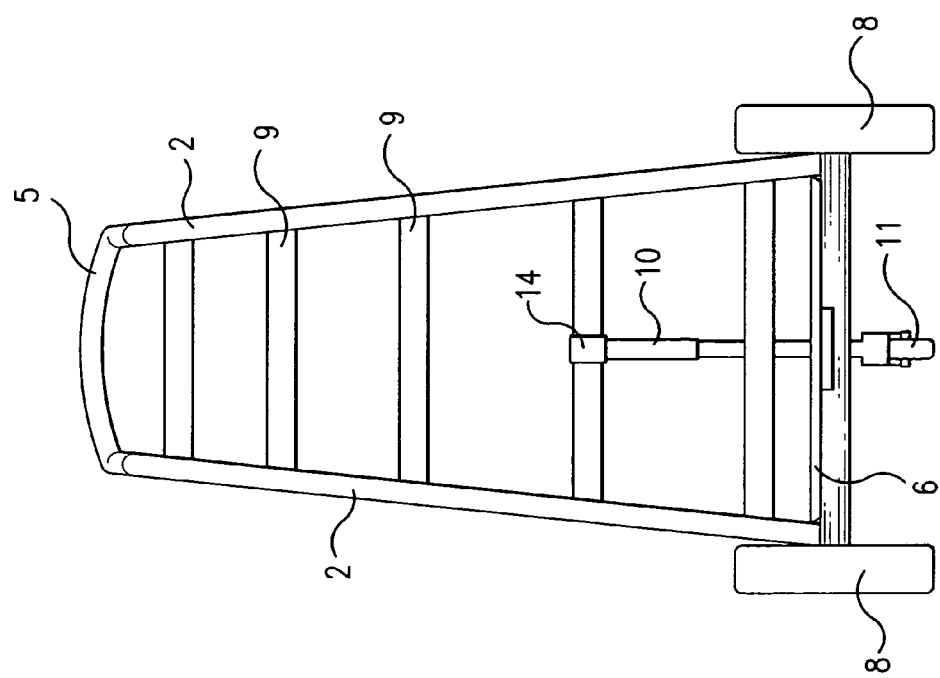
FIG. 3 is a full back view of the device without panel or tracks.

Also shown in FIG. 2 is an extended (telescopic) wheel bar 10 and wheel 11 for the wheel bar 10. The extended wheel bar 10 has a distal end 12 and a near end 13 and the wheel 11 is rotatably mounted on the distal end 12. The near end 13 is fastened to a cross member 9 at the back of the device 1. It is fastened by being rotatably attached to a welded hinge plate 14 that is attached to the cross member 9. Thus, the wheel bar 10 and the wheel 11 are designed to collapse and fit up against the cross member 9 for storage as shown in FIG. 1. FIG. 3 is a full front view of the device 1.

Figure 4:
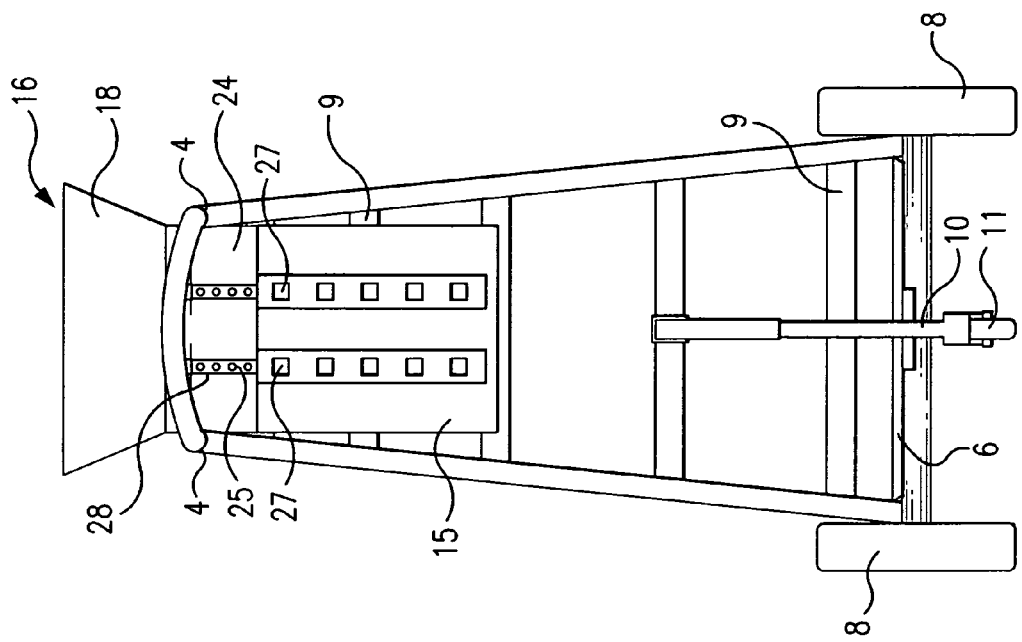
FIG. 4 is a full back view of the device showing panel and tracks.

FIG. 4 is a full back view of the device 1 in which like numbers refer to like components as shown in FIGS. 1 and 2.

Also shown is a back plate 15 fixedly mounted on the back of the device 1 and near the distal ends 4 of the strut 2. The back plate 15 forms of the novel system for adjusting the funnel 16, wherein the detail of the funnel 16 will be described infra. The back plate 15 has two parallel, adjacent, evenly spaced, vertical tubular rails 17 attached to it. Each vertical tubular rail has vertically aligned openings 27.

Figure 11:
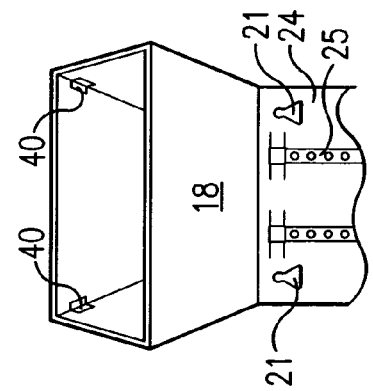
FIG. 11 is a full view of the spring clips.

The funnel 16 is removable. Aside from the funnel top 18, the funnel 16 is comprised of four, lower vertical panels 19 that are hinged onto the bottom edges 20 of the funnel top 18 by hinges that will be discussed infra. The panels 19 form a box-like structure 23 (see FIG. 8B) on the bottom of the funnel top 18. The panels 19 have attached to them, spring clips 21 (see FIG. 11), that are mounted on the outside surface of the lower vertical panels 19, and are used for holding a trash bag 22 (FIG. 1) on the funnel 16.

Shown in FIG. 4 is a back panel 24(19), which is the back panel of the box-like structure 23. The back panel 24 has fixedly mounted on it, parallel, spaced-apart, bars 28 (see FIG. 5) that have vertical clips (or buttons) 25 attached to them, that align with and have the width of the openings 27 on the back plate 15.

The bars 28 are attached to the back panel 24 as shown in FIG. 6, wherein it is shown that the bars 28 are affixed at the top 29 of the bar 28. The side panel of the vertical tubular rail 26 has been removed so that the relationship of the bar 28 and the vertical tubular rail 26 can be illustrated.

In use, the bar 28 with the vertical clips 25 inserts into the vertical tubular rail 26, and the vertical clips 25 insert into openings 27 in the back plate 15 and hold the funnel 16 and box-like structure 23 in place. To adjust the funnel 16, the clips 25 are removed from the openings 27 by pressing on the back plate 15 and elevating or dropping the funnel 16, until the desired height is obtained, and then the buttons or clips 25 are re-inserted back into the openings 27. FIG. 7 is a full top view of the combination of the bar 28 and the vertical tubular rail 26.

The details of the back plate 15 and the vertical clips or buttons 25, and the back panel 24 and the openings 27 can best be viewed in FIG. 5, which is an enlarged view of said panel and plate.

FIG. 6 illustrates the alignment and interface between the back plate 15 and the vertical clips 25, and the back panel 24 and the openings 27. It should be noted that the buttons or clips 25

In this manner, the trash bag 22 can be filled sequentially from bottom to top without worrying about the trash bag 22 slipping or moving on the device.

The adjustable, extendable bar wheel 10 is affixed to a middle cross member 9 at the back of the back plate 15 which allows the easy transport of the device 1. When the clean up job is finished, or when the trash bag 22 is full, then the device will allow the easy transport to the street or any other denoted dumping site for the trash.

To facilitate the handling of the trash bag 22, and to ensure that the trash bag 22 remains with the device 1 during transport, there is used a strap 37, shown in FIG. 1.

Figure 10:
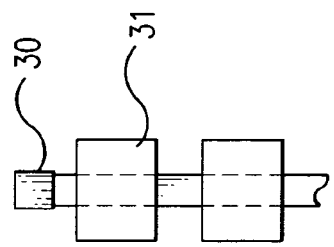
FIG. 10 is a detailed view of the novel fastener for the funnel panels.
Figure 9:
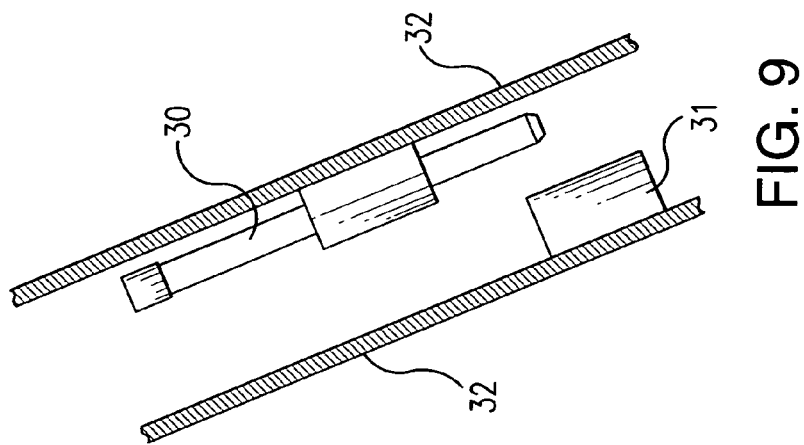
FIG. 9 is a detailed view of the novel fastener for the funnel panels.

Turning now to a detailed discussion of the funnel 16, reference is made to FIGS. 8A and 8B wherein it is shown in FIG. 8A the funnel 16, showing the funnel top 18 in cross-section taken from FIG. 5, through line A-A, and back panel 24. The cross sectional funnel shows one mode of the interior fastening devices for the four components of the funnel top 18 which are bolts 30, and receivers 31 for the bolts, which, as can be observed from the enlargement FIGS. 9 and 10. FIG. 9 shows two of the funnel components 32 being brought together to fasten with the bolt 30. It is contemplated within the scope of this invention to fasten the funnel components together using hinges for collapsibility purposes. It is also contemplated within the scope of this invention to use magnets 40 (FIG. 8A) to secure such funnel components. The funnel components 32 also have a hinge 40, that hinges the funnel components 32 to each other (See FIG. 8A).

Figure 12:
FIG. 12 is a full view of the rod handle of the compactor.
Figure 13:
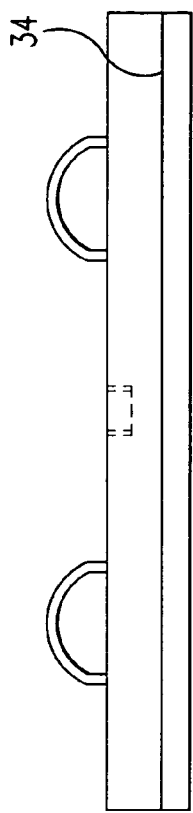
FIG. 13 is a full front view of the platform of the compactor.
Figure 15:
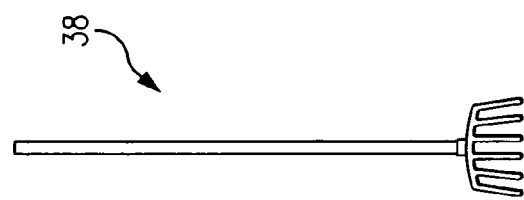
FIG. 15 is a full view of the collapsible rake of this invention.
Figure 14:
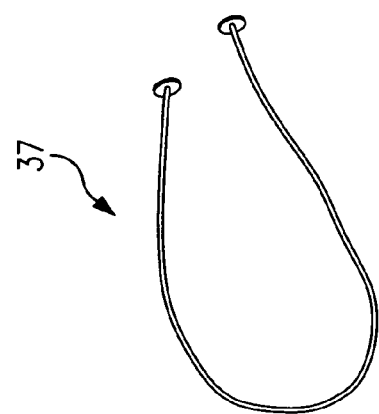
FIG. 14 is a view of a strap for holding a bag in place.

As the trash bag 22 is filled, one can use the rod compactor set forth in FIGS. 12 and 13, wherein FIG. 12 illustrate a rod-like handle 33 which, for illustration purposes, threadedly connects to the platform 34 to form the rod compactor 35, is used to tamp down and compact the trash in the trash bag 22. Also shown in FIG. 14 is an illustration of a strap 37 to hold the trash bag 22 on the device 1 while trash bag 22 is being transported. Finally, there is an adjustable rake 38 that is capable of being mounted on the device 1.

Figure 16:
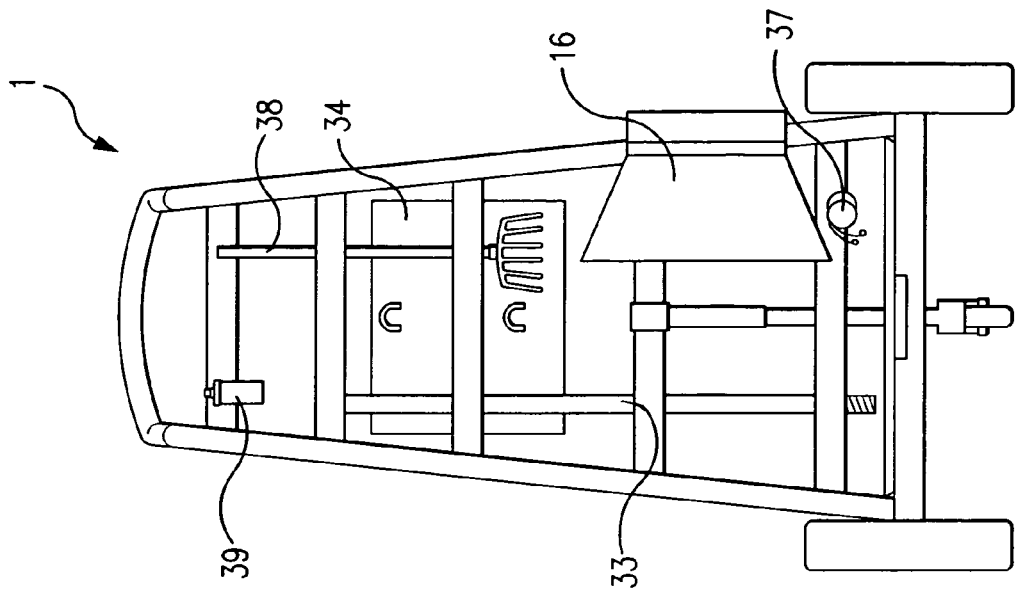
FIG. 16 is a full front view of the device of this invention that is equipped with all of the accessories for lawn work.

FIG. 16 shows a device 1 of this invention fully loaded with accessories. Shown are water bottle 39, the rake 38, the platform 34, the rod compactor handle 33, the funnel 16 with panels 19 fully collapsed, and a strap 37.

Figure 17:
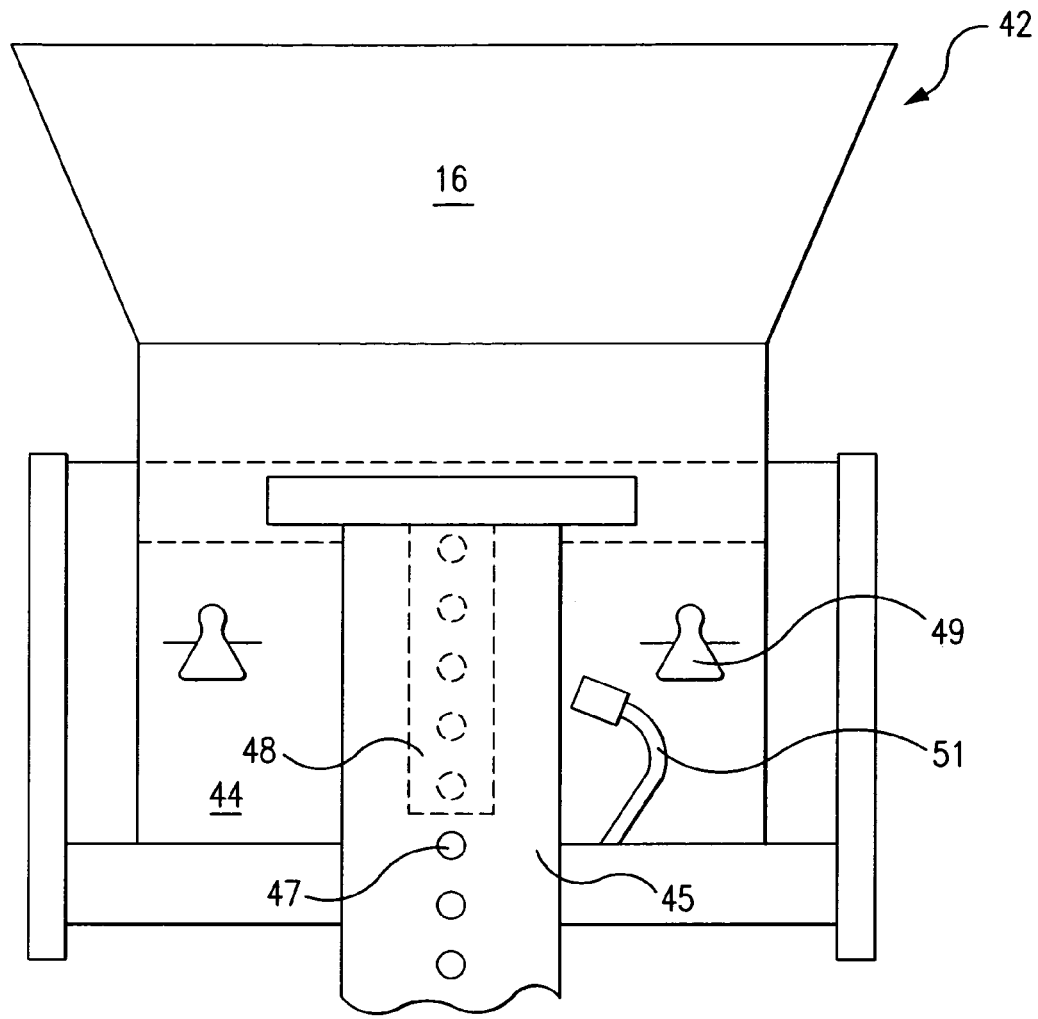
FIG. 17 is a full back view of another embodiment of this invention.
Figure 18:
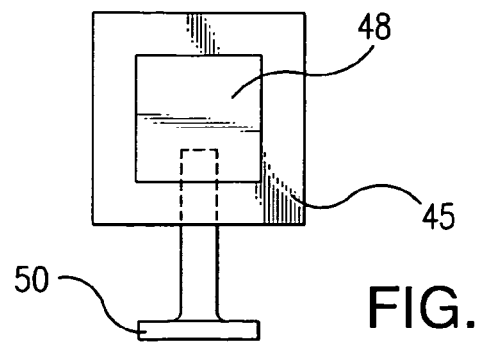
FIG. 18 is a full top view of the single bar embodiment.

Turning now to another embodiment of this invention there is shown in FIG. 17 a device 42 which has only a single rail 43 adjustment means as opposed to the double rail adjustment means of the first embodiment.

Thus, shown in FIG. 17 is the device 42 (top portion shown), along with the funnel 47, the spring clips 49 that hold the trash bag, the vertical tube 45, and the single rail 48.

There are openings 52 in the single rail 48, and openings 53 in the vertical tube 45 and these align with each other. The single rail 48 and the vertical tube 45 are held in place by the insertion of a pin 51 through both holes. To adjust, the pin is removed and the funnel 16 with the single rail 48 is moved up or down to accommodate the desired height and then the pin 51 is re-inserted through the holes to hold them in place.

The devices 1 and 42 of this invention and its accessories are manufactured from aluminum, plastics, or carbon fiber impregnated resins, or a combination of them.

The devices of this invention, i.e., a lawn caddy is for receiving and transporting waste such as grass clippings, leaves, plant vegetation and compost waste. The lawn caddy transports yard waste from one location to another without heavy lifting. It is light and durable, having a maximum weight of 10 to 12 pounds with a capacity to hold 40 pounds or less of yard waste. By filling refuse bags and transporting waste to a curb side shortens time spent in cutting and cleaning lawns.

What is claimed is:

1. A portable lawn caddy, said lawn caddy comprising in combination:
   a. two adjacent, spaced-apart, parallel struts, each said strut having a near end and a distal end, each said strut having a handle at said distal end;
   b. said distal ends being joined by a flat platform;
   c. said distal ends having an axle through them, each of said ends of said axle being fitted with a rotatable wheel;
   d. there being a plurality of cross members extending from one said strut to said other strut;
   e. there being a back plate mounted near said distal ends of said struts, said back plate having a parallel set of vertical tubular rails attached thereto, each said vertical tubular rail having openings therethrough, wherein said openings are adjacent and evenly spaced in vertical rows;
   f. there being a removable funnel having a funnel top, said funnel top having bottom edges, there being mounted on said bottom edges, panels, said panels configured to provide a box-like structure, said panels having mounted on an outside surface, spring clips for holding a trash bag;
   g. a back panel of said box-like structure having fixedly mounted thereon, parallel, spaced-apart, vertical bars, each said bar having vertical clips attached thereto, said vertical clips aligning in width with said openings in said vertical tubular rails, each said vertical bar being insertable in one of said vertical tubular rails;
   h. there being an adjustable, extendable bar wheel affixed to a middle cross member, at said back of said back plate.

2. The lawn caddy as claimed in claim 1 wherein the mounting of said funnel panels on said funnel is rigid.

3. The lawn caddy as claimed in claim 1 wherein said funnel panels are mounted on said funnel with hinges.

4. The lawn caddy as claimed in claim 1 wherein said lawn caddy is manufactured from a material selected from said group consisting of aluminum, plastic, and carbon fiber filled resins.

5. The lawn caddy as claimed in claim 1 wherein said wheels are at least three inches in diameter.

6. A portable lawn caddy, said lawn caddy comprising in combination:
   a. two adjacent, spaced-apart, parallel struts, each said strut having a near end and a distal end, each said strut having a handle at said distal end;
   b. said distal ends being joined by a flat platform;
   c. Said distal ends having an axle through them, each of said ends of said axle being fitted with a rotatable wheel;
   d. there being a plurality of cross members extending from one said strut to said other strut;
   e. there being a back plate mounted near said distal ends of said struts, said back plate having a single, essentially centered, vertical tubular rail attached thereto, said vertical tubular rail having openings therethrough, wherein said openings are evenly spaced in a vertical row;
   f. there being a removable funnel having a funnel top, said funnel top having bottom edges, there being mounted on said bottom edges, panels, said panels configured to provide a box-like structure, said panels having mounted on an outside surface, spring clips for holding a trash bag;
   g. a back panel of said box-like structure having fixedly mounted thereon, a vertical bar, said bar having vertically aligned openings therethrough, said vertically aligned openings aligning with said vertically aligned openings in said vertical tubular rail, said vertical bar being insertable in said vertical tubular rail;
   h. there being an adjustable, extendable bar wheel affixed to a middle cross member, at said back of said back plate.

* * * * *